United States Patent
Kloth

[11] Patent Number: 5,833,630
[45] Date of Patent: Nov. 10, 1998

[54] SAMPLE COLLECTION DEVICE

[76] Inventor: Bernd Kloth, Müssenredder 8, D-22399 Hamburg, Germany

[21] Appl. No.: 792,469

[22] Filed: Jan. 30, 1997

Related U.S. Application Data

[63] Continuation of Ser. No. 359,514, Dec. 20, 1994, abandoned.

[30] Foreign Application Priority Data

Nov. 3, 1994 [DE] Germany ............... 9417612 U

[51] Int. Cl.⁶ .................................................. A61B 5/00
[52] U.S. Cl. ............................................................ 600/576
[58] Field of Search ..................... 600/573, 576, 600/583, 584; 606/181; 604/36, 37, 51, 181

[56] References Cited

U.S. PATENT DOCUMENTS

| | | | |
|---|---|---|---|
| 3,908,638 | 9/1975 | Porcher et al. .................. | 128/763 |
| 4,024,857 | 5/1977 | Blecher et al. ................... | 128/763 |
| 4,215,700 | 8/1980 | Crowther et al. ................ | 128/763 |
| 4,227,620 | 10/1980 | Conway ............................ | 128/763 |
| 4,298,011 | 11/1981 | Mangurten et al. ............... | 128/763 |
| 4,420,254 | 12/1983 | Smeaton ............................ | 356/246 |
| 4,576,185 | 3/1986 | Proud et al. ....................... | 128/760 |
| 4,589,421 | 5/1986 | Ullman .............................. | 128/763 |
| 5,257,984 | 11/1993 | Kelley ............................... | 128/763 |
| 5,267,152 | 11/1993 | Yang et al. . | |
| 5,341,291 | 8/1994 | Roizen . | |

FOREIGN PATENT DOCUMENTS

| | | | |
|---|---|---|---|
| 0 421175 | 4/1991 | European Pat. Off. . | |
| 63-078043 | 8/1988 | Japan . | |
| 6197887 | 7/1994 | Japan ................................. | 128/760 |
| WO 79/01131 | 12/1979 | WIPO . | |

*Primary Examiner*—Max Hindenburg
*Attorney, Agent, or Firm*—Donavon Lee Favre

[57] ABSTRACT

In order to provide a sample collection device (100) for the collection of capillary blood directly from the patient or for taking a sample from a liquid with the aid of a capillary (16) so that it is made possible to perform analyses of the sample free from volume errors within the sample area and free from contamination, it is proposed that the capillary (16), for the absorption of sample liquid to be analyzed, be connectable with the aid of a mounting means (100) with a cuvet (10) possibly containing a reagent liquid.

20 Claims, 3 Drawing Sheets

SAMPLE COLLECTION DEVICE

This application is a continuation of Ser. No. 08/359,514 filed Dec. 20, 1994, now abandoned.

DESCRIPTION

The present invention relates to a sample collection device for the collection of capillary blood from the patient directly or for taking a sample from a liquid with the aid of a capillary.

BACKGROUND OF THE INVENTION

Capillary blood collections are frequently performed in clinical medicine. For this purpose, a finger pad, the lobe of an ear or, in the case of babies and infants, the heel is punctured with a lancet. Since tissue thrombokinase issues together with the blood, the first drop of blood is removed and discarded so as to prevent the following analysis from being distorted. The blood which subsequently issues is collected with the aid of a pipet which is provided with a tube and a mouthpiece in order to enable the person taking the blood sample to draw in the blood by suction. Following this the blood is transferred into a cuvet by the pipet being blown out. However, this method holds numerous sources of error since it is impossible to measure the volume of the sample liquid with the requisite degree of accuracy. This is due to the direct connection of the column of air above the blood in the pipet with the person collecting the blood sample. Moreover, the possibility of the sample being contaminated by the respiratory air of this person which carries humidity and germs, cannot be ruled out. The other way around, too, the risk of infection exists for the person taking the blood sample if the blood were to inadvertently reach the mouth via the tube from the pipet. In addition, this method is not suitable for automated analysis methods since a clearly defined starting time cannot be obtained when the blood is blown out. It is also possible for a strong bubble and/or foam formation to start owing to the blowing out, which likewise distorts the measurement results significantly.

In order to at least partially eliminate these flaws, it has been proposed according to the publication DE-AS 24 22 260, to operate with end-to-end capillaries, in which case the sample volume is defined here by means of the length and cross-section of the capillary. The capillary brought up to the drop of blood at a suitable angle, whereupon the capillary is automatically drawn full of blood by virtue of the capillary action. The capillary, together with the blood contained therein, is transferred into a cuvet and the same is closed with a cap. An intermixing of the sample is effected by means of a careful tilting of the cuvet. This method makes a contamination-free sample praparation with a defined volume possible. Although it is strived for in the above-identified publication that the capillary is to adhere to the inside of the cuvet wall during the measuring process, it has been shown though in practical operation that the cuvet is nevertheless often found located in the measuring channel and thus has a serious negative influence on the measurement. This does occur, inter alia, owing to carelessness on the part of the operating staff and also on account of a defective capillary which, due to an irregularity in its surface, is incapable of adhering to the wall. Also in the case of this method a clearly defined starting time for an automated measurement method cannot be adhered to so that only a limited scope of application is available.

That is why the technical problem of the present invention is to provide a sample collection device which makes it possible to obtain sample analyses which are free from volume errors within the sample region and free from contamination. In addition, it is intended that a clearly defined starting time for an automatic reaction start be provided.

SUMMARY OF THE INVENTION

In this invention the capillary is held directly into the cuvet provided for the analysis so that the sample liquid, more particularly blood, is absorbed by capillary action by means of the capillary in the form of a defined sample volume and subsequently transferred into the cuvet for the start of the analysis.

A cuvet is provided on this occasion with a reagent and, if necessary, also with an agitating member in the form of a small bar or rod or a sphere and is closed with the aid of a cuvet cap that can be either plugged or screwed on. In lieu of the cap, it is also possible to employ a foil that adheres firmly to the edge of the cuvet. Prior to the analysis being performed, the cap is removed or the foil drawn off. Following this, the cuvet is immediately provided with the capillary holder which, by preference, is constructed in the form of a cap for the cuvet. For this, a cuvet is fitted with a capillary holder which fixates the capillary in the cuvet aperture in such a way that the same is not immersed in the reagents.

In the capillary holder, the capillary is preferably disposed in such a way that it projects somewhat with its end from the capillary holder so as to enable a problem-free sample absorption to take place. To this end, the capillary is, with the adhering cuvet, brought up to the sample in such a way that the sample volume is absorbed by the capillary action.

It is possible to make provision for the cuvet, together with the capillary, prior to the absorption of the sample, to be inserted into a heating device, for example, into the analyzer so as to be subjected to a preheating of e.g. 37° C.

Both with the absorbed sample as well prior to the absorption of the sample, the capillary/cuvette combination is absolutely safe to handle since a leakage of reagent from the cuvet is prevented with certainty by means of the cap and a leakage of sample liquid by the capillary forces. Provision is made furthermore for the other end of the capillary to project somewhat into the cuvet and this only to such an extent that the capillary end does not come in contact with the surface of a possibly filled-in reagent and is disposed at a distance therefrom. In this fashion it is also safely prevented that reagent liquid penetrates the capillary.

For starting the planned analysis, the sample liquid is transferred into the cuvet. For this purpose it may be provided that the capillary aperture which faces away from the cuvet can be acted upon with compressed gas with the aid of a means which is a component or a supplementary part of the blood sample collection device in such a way that, between the aperture facing away from the cuvet and the aperture of the capillary facing toward the cuvet, a defined pressure difference prevails, this pressure difference being regulated in such a way that, by the evacuation of the sample liquid into the cuvet, owing to the pressurization, the pressure difference is compensated or possibly that a small quantity of gas will likewise be discharged. A precisely defined sample volume is transferred devoid of contamination into the cuvet. By preference, it is provided that the volume in the pressure cap is regulated in such a way that, when placing the pretective cap on the extension and subsequently pressing the same completely down, the sample liquid is forced just out of the capillary. It is possible, therefore, by a simple placing in position and depression of the pressure cap, to effect the evacuation of the capillary or the filling of the cuvet. To this end provision is made according to the invention for providing a blood collection device with integrated cuvet for analysis purposes, in which case the cuvet holds reagent liquids, as well as with a capillary that can be filled with a pressure and protective cap, with the aid of which a defined air volume can be urged through the capillary in such a fashion that the sample liquid or the blood is capable of issuing into the cuvet devoid of any bubble and/or foam formation.

The capillary with holder can also be employed without any connection to the cuvet for the collection of samples. The thusly filled capillary is then placed upon the cuvet coated with reagent. The capillary holder on the attachable side of the cuvet has to be constructed in such a way that, when the holder is placed in position, the air is able to escape laterally between the cuvet rim and the holder. Consequently all the liquid remains in the capillary, following this the starting operation will take place as described with the pressure cap.

When the pressure cap is depressed, the free end of the capillary is likewise pressed down and this in such a way that the end is pushed completely into the through bore of the capillary holder or of the extension. Hereby the other end is pushed out further at the same time so that it now reaches as far as into the reagent or sample liquid.

In the course of the subsequent agitating operation, the sample residue possibly still adhering at the end of the capillary on the inside and the outside is rinsed off so that it is achieved with absolute certainty that the planned sample volume reaches the inside of the cuvet and is intermixed with the reagent.

For special purposes provision can be made for the capillary to be internally coated with an anticoagulant so that an absorbed sample will not coagulate. It is thus made possible that the collection of the sample and the analysis can be performed at different times.

In the center of the capillary holder a cylindrical extension is located, in which the capillary is disposed in a through bore. The protective and pressure cap is placed on this extension, in which case the extension and the outwardly projecting capillary project into the interior of the protective cap. By moving the protective cap in the direction of the capillary holder or the cuvet, the air remaining in the protective cap is compressed since the extension and the protective cap act like a pump piston and a piston housing. Due to this, a defined pressure lies on the capillary aperture in the bore of the protective cap, whereby the blood is urged from the capillary into the cuvet and this in such a way that solely the sample liquid and, possibly, an insignificant quantity of air enters the cuvet from the capillary. The quantity (volume) of air possibly issuing together with the sample liquid has to be regulated in such a fashion that no bubble and/or foam formation takes place. According to a preferred embodiment this is $1/10$ to $1/2$ of the volume of the capillary.

Advantageously the capillary holder, toward the cuvet side, on the contact surfaces in the direction of the cuvet rim, is provided with grooves through which the air is able to escape from the cuvet so that no excess pressure can build up in the cuvet. The cuvet may be configured in any way whatever so as to meet the requirements determined by the analyzer.

According to a certain embodiment, it is likewise advantageously provided to close the cuvet with a foil, a turn-lock closure means or a cap so as to render it proof to evaporation. It is possible thereby prevent errors due to the evaporation of the reagents when left standing over prolonged periods. When the capillary holder is attached, the closure means or the foil is removed or destroyed, respectively.

A further mode of approach is to fill the cuvet with a defined quantity of an anticoagulant buffer mixture, in this case a citrate buffer, and to transfer the sample into the same as described. In this manner it is possible to maintain the sample stable for up to 24 hours and to consequently also perform the analysis at a location other than the one where the blood was collected. In order to trigger a reaction start, the capillary is removed from the cuvet and the staring reagent is supplied to the sample with the aid of a pipet.

Owing to the construction according to the invention with capillary holder and protective cap, it is possible following the performed analysis to dispose the sample together with the cuvet tightly closed in the garbage without fearing any risk of infection.

That is why the sample collection device according to the invention is particularly suitable for automated analyses which it is possible to perform by a person possessing no previous medical training, by way of example, a patient who has to take a medication for inhibiting blood coagulation. It is possible, however, for every type of liquid samples to be collected for the most widely varied analyses and to be supplied to an analyzer.

The sample collection device is then employed as detailed below:

For the taking of a blood sample, the capillary/cuvet combination is held at a suitable angle to the drop of blood, whereupon the capillary is filled automatically. By the application of the protective cap, the air is urged through the capillary and the blood enters the cuvet filled with reagents. On account of the blood entering the reagent; it is possible, depending on the analyzer in question, to start the analysis automatically and the desired measured data, such as e.g. the coagulation time, can be determined.

BRIEF DESCRIPTION OF THE DRAWINGS

Further advantageous constructions are explained with the aid of drawings. Thus

DETAILED DESCRIPTION OF THE PREFERRED EMBODIMENT

Figure 1:
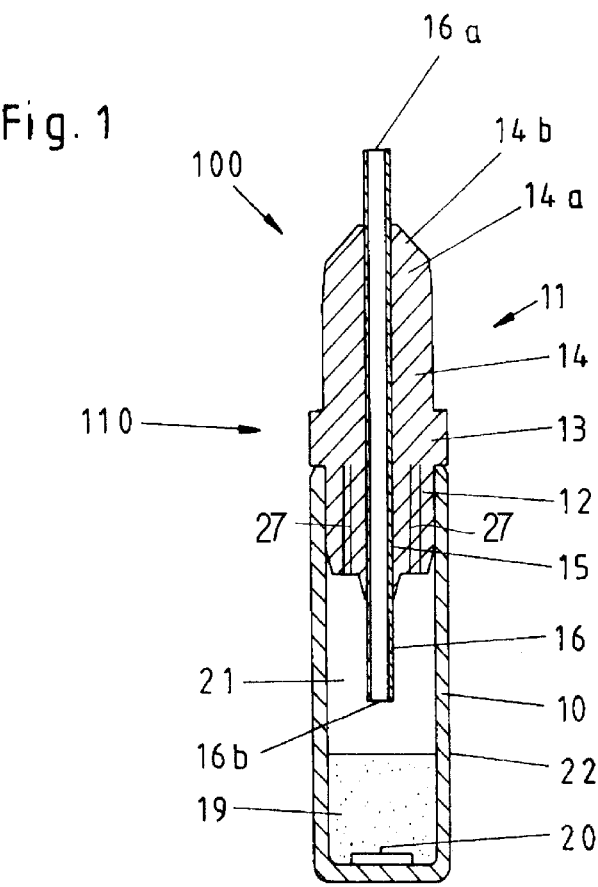
FIG. 1 shows the sample collection device in a vertical sectional depiction.

The blood collecting device 100 illustrated in the FIGS. 1 through 8 is provided with a cuvet 10 which is sealed with the aid of a capillary holder 11. This capillary holder 11, in the direction toward the cuvet 10, possesses a plug-like section 12 which extends into the cuvet 10 and thereby produces the closure means.

The capillary holder 11 engages around the cuvet 10 with the aid of a circumferential rim 13 which can be pulled down on the outside 22 of the cuver 10. On the capillary holder 11, located opposite the plug-like section 12, an extension 14 is disposed, through which, as also through the plug-like section 12, a through bore proceeds, into which the capillary 16 is inserted. A protective and pressure cap 17 can be applied to the extension 14. For this, on the extension 14, at the free end 14a, a circumferential bevel 14b is formed in order to facilitate the application of the protective and pressure cap 17 to the extension 14.

The region of the protective and pressure cap 17 into which the extension 14 projects possesses an internal diameter I which corresponds to the external diameter A of the extension 14 so that the extension 14 is displaceable in the protective and pressure cap 17 in the manner of a pump piston in a pump housing. The internal volume 23 of the protective and pressure cap 17 can be regulated by means of the variation in the depth in such a way that the air remaining in the internal volume 23 after the application of the protective cap just suffices for expelling the sample into the cuvet. The air which remains in the protective and pressure cap 17 is compressed in the process so that, in the interior of the protective cap, a higher pressure prevails than in the environment or in the cuvet 10.

Therefore, the aperture 16a of the capillary 16 which faces away from the cuvet 10 is pressurized so that, between the aperture which faces away from the cuvet 10 and the aperture 16b of the capillary which faces toward the cuvet 10, a pressure difference exists. This pressure difference is defined by a suitable selection of the volume of the pressure and protective cap 17, and this in such a way that, after the evacuation of the sample liquid into the cuvet 10, due to the pressurization of the aperture 16a, the pressure difference is just compensated or a small quantity of air likewise escapes. However, this quantity of air may only be such that no formation of bubbles and/or foam takes place. Reagent liquid 19 as well as an agitator member 20 are disposed in the cuvet 10.

Figure 3:
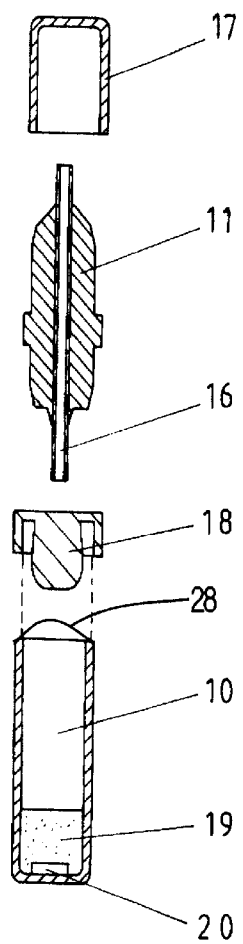
FIG. 3 shows, in an exploded view, the sample collection device according to FIG. 1 with a cuvet closure means to be removed prior to the attachment of the capillary holder.

In FIG. 1 it is illutrated how the sample collection device comprised according to the invention of the cuvet 10, the capillary holder 11 and the capillary 16, is used for taking a blood sample issuing from a digital pulp. For this—as indicated in FIG. 3—the cuvet cap means 18 has been removed to start with and, following this, the capillary holder 11 with the capillary 16 mounted by the same has been placed in position.

It is also possible for the protective and pressure cap 17 to be substituted in its function by the cuvet cap 18 which, in its interior, has to be designed in the way described for the protective and pressure cap 17.

Figure 4:
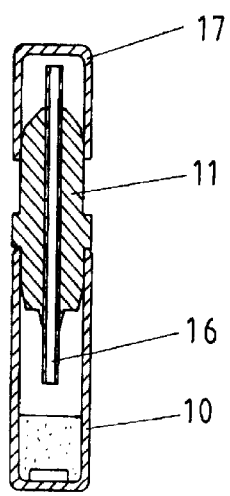
FIG. 4 shows, in a vertical sectional depiction, the sample collecting device with a pressure and protective cap applied, in a first position.

Following the collection of the blood sample, the protective and pressure cap 17 is applied in a first position illustrated in FIG. 4. The first pressure increase brought about in the process in the protective and pressure cap 17 still is in equilibrium with the capillary forces in the capillary so that the sample disposed in FIG. 4 and not depicted in the drawing does not issue as yet. It is then possible to readily convey the sample to an analyzer.

Figure 5:
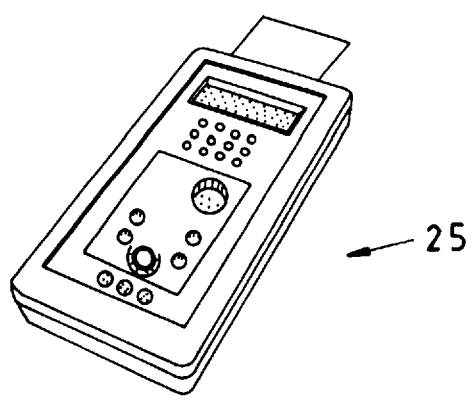
FIG. 5 shows, in a diagrammatical view, an analyzer provided for the sample collection device.
Figure 6:
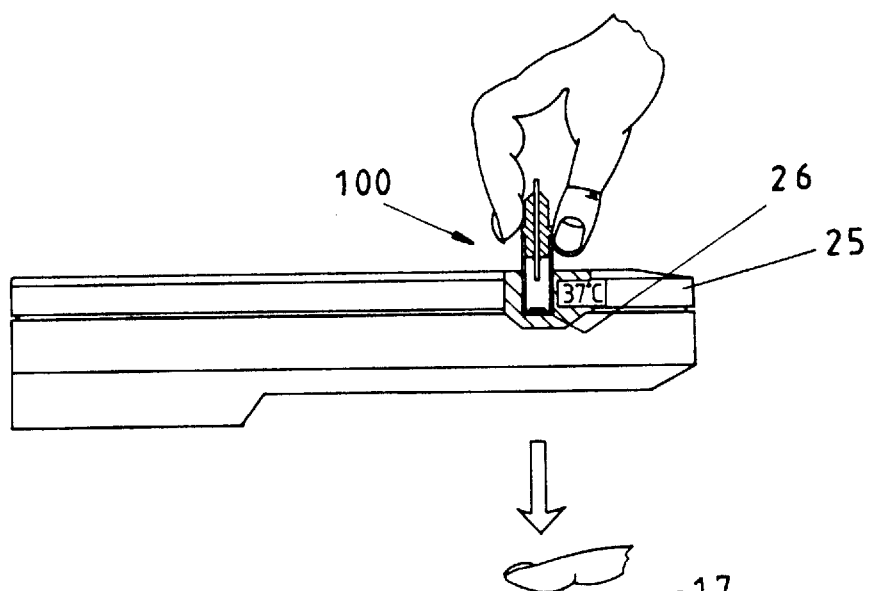
FIG. 6 shows, in schematic depiction, the insertion of the sample collection device into an analyzer.
Figure 7:
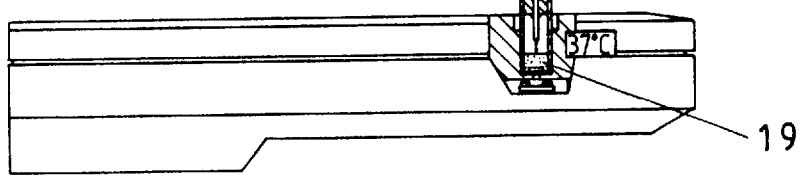
FIG. 7 shows, in schematic depiction, the handling of the sample collection device with an analyzer.
Figure 8:
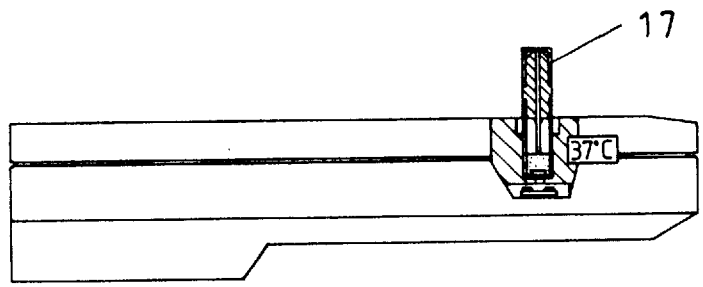
FIG. 8 shows, in schematic depiction, the starting of the analysis of the sample collection device in the analyzer.

An analyzer 25 that is particularly suitable for persons lacking any previous medical training is shown in FIG. 5. The device to be prepared for the collection of a sample can be made ready in the same in that it is inserted into the measuring canal 26 and heated therein to the necessary temperature, e.g. 37° C. (FIG. 6).

Figure 2:
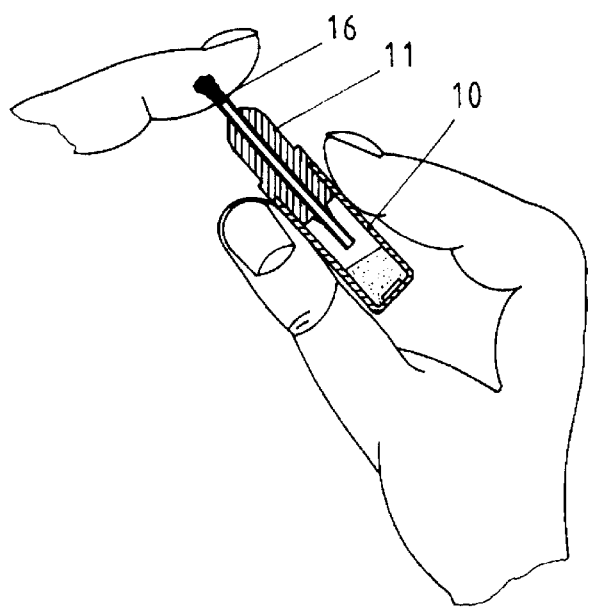
FIG. 2 shows a blood collection being performed with the sample collection device according to FIG. 1 in a diagrammatical view.

After the collection of the sample and the application of the protective and pressure cap 17 as per FIGS. 2 and 4, the sample collection device 100 is inserted into the analyzer 25. Here, by depressing the protective and pressure cap 17, the sample, e.g. capillary blood, is pressed into the cuvet 10 or into the reagent liquid 19. By the change in the light transmittance of the reagent liquid 19, due to the blood or the sample supplied, the analysis is automatically started (FIG. 8), so that the analysis conditions remain constant at all times. By preference it may be provided that the analyzer 25 stores the results of the analysis in an internal memory.

| LIST OF REFERENCE NUMBERS | |
|---|---|
| Sample collection device | 100 |
| mounting means | 110 |
| cuvet | 10 |
| capillary holder | 11 |
| plug-like section | 12 |
| rim | 13 |
| extension | 14 |
| free end | 14a |
| bevel | 14b |
| through bore | 15 |
| capillary | 16 |
| capillary apertures | 16a, 16b |
| protective and pressure cap | 17 |
| cuvet cap | 18 |
| reagent liquid | 19 |
| agitator member | 20 |
| interior | 21 |
| exterior | 22 |
| internal volume | 23 |
| analyzer | 25 |
| measurement canal | 26 |
| grooves | 27 |
| evaporation-proof foil | 28 |

What is claimed is:

1. A sample collection device for the collection and analysis of the coagulation time of capillary blood taken directly from a patient with the aid of a capillary, comprising a unitary combination of a) through f):

a) a capillary for the capillary attraction into the capillary of a predetermined quantity of blood to be analyzed directly from the patient;

b) a cuvet;

c) a reagent liquid contained within said cuvet;

d) an agitator member contained within said cuvet and surrounded by said reagent liquid;

e) a means for mounting said capillary, said mounting means comprising:

a capillary holder, said capillary holder retaining said capillary in a position disposed on said cuvet and extending into said cuvet with a plug-like section of said capillary holder, said capillary holder possessing an extension on the side facing away from said cuvet in the center of said capillary holder; and f) a protective and pressure cap longitudinally displacable on and in pressure sealable relationship with said extension of said capillary holder, the downward movement of the pressure cap creating a gas pressure in the capillary which forces blood in the capillary into the reagent;

g) a measuring canal for the cuvet; and h) an analyzer having an internal memory, the analysis process of which is activated by entry of blood into the cuvet; and i) recording the coagulation time of the blood in the internal memory of the analyzer.

2. A sample collection device according to claim 1 wherein a through bore extends through the capillary holder:

said capillary is mounted in said capillary holder so as to be longitudinally displacable into the reagent by the downward movement of the pressure cap.

3. A sample collection device according to claim 1, wherein said cuvet is sealed with the aid of said capillary holder.

4. A sample collection device according to claim 1, wherein said protective and pressure cap is constructed so as to be placeable into a first position engaging only partially over said extension and into a second position in which it can be slid forward so as to engage completely over said extension.

5. A sample collection device according to claim 1, wherein withing a contact area of said plug on said cuvet or within only a contact area of said extension under the pressure cap before the cap is depressed, or both, grooves are constructed in the direction toward said cuvet which permit a pressure compensation between the interior of said cuvet and the external environment when the pressure cap is depressed.

6. A sample collection device according to claim 1, wherein said circumferential rim of said capillary holder is moved downwardly in the direction of said cuvet on the exterior of said cuvet.

7. A sample collection device according to claim 1, wherein an aperture of said capillary on the side facing away from said cuvet can be acted upon by a compressed gas with the aid of a means which forms part of or is a supplementary part of said sample collection device, in such a way that, between said aperture on the side facing away from said cuvet and an aperture on the side facing toward said cuvet of said capillary, a defined pressure difference exists, said defined pressure difference is regulated in such a way that, by the evacuation of a sample liquid into said cuvet, the pressure difference is compensated by the pressurization of a small quantity of gas that escapes.

8. A sample collection device according claim 7, wherein said small quantity of gas corresponds to the volume of said capillary, preferably 1/10 through 1/2 of the volume.

9. A sample collection device according to claim 7, wherein said small quantity of gas is air.

10. A sample collection device according to claim 1, wherein the volume in said protective and pressure cap is regulated in such a way that, when said protective and pressure cap is placed upon said extension and is subsequently pressed down completely, a sample liquid is urged out from said capillary.

11. A sample collection device according to claim 1, wherein said cuvet, when separated from said capillary holder, is sealed by means of an evaporation-proof foil or a detachable cuvet cap.

12. A sample collection device according to claim 11, wherein said cuvet cap can be employed as a pressure cap and is constructed so as to be placeable into a first position in which it engages only partially over said extension and into a second position, in which it engages completely over said extension.

13. A sample collection device according to claim 12, wherein an internal volume in said cuvet cap constructed in the form of a pressure cap is regulated to urge a sample liquid from said capillary when said cuvet cap is placed on said extension and when subsequently depressed completely.

14. A sample collection device according to claim 1, wherein an anti-coagulant, such as a citrate buffer, is contained in a reagent liquid in said cuvet.

15. A sample collection device according to claim 1, wherein said capillary is an end-to-end capillary.

16. A sample collection device according to claim 1, wherein a through bore in said capillary holder is shorter than the length of said capillary.

17. A sample collection device according to claim 16, wherein said through bore in said capillary holder is 20% to 30% shorter than the length of said capillary.

18. A sample collection device for the collection of an accurately measured amount and analysis of capillary blood taken directly from a patient or from a liquid with the aid of a capillary, comprising a unitary combination of a) through e):

a) a capillary for the absorbtion by capillary attraction of an accurately measured amount of sample liquid to be analyzed, b) a cuvet;

c) a means for mounting said capillary on said cuvet; and d) a pressure cap means for creating a pressure at one end of the capillary which transfers the blood in the capillary into the cuvet; and e) a means for analyzing said sample liquid within said cuvet without removing said capillary and mounting means.

19. A unitary sample collection device comprising the assembly of a) through e):

a) a cuvette wherein the pressure in the cuvet is atmospheric;

b) a plug in the cuvette;

c) a through bore through the plug;

d) a longitudinally displacable pressure cap for the plug having a travel path over an end of the plug to create a pressure; and e) a capillary in the through bore.

20. The sample collection device of claim 19 wherein contents of the cuvet from an end of the capillary in the cuvet to a terminal end of the cuvet opposed to the plug consist essentially of air, reagent and a stirring member, free of a restraining membrane.

* * * * *